US00PP31817P3

(12) United States Plant Patent
van Langen

(10) Patent No.: US PP31,817 P3
(45) Date of Patent: May 26, 2020

(54) ***HAWORTHIA* PLANT NAMED 'AMIHAW1616'**

(50) Latin Name: ***Haworthia limifolia* x *Haworthia pentagona***
Varietal Denomination: AMIHAW1616

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 16/501,201

(22) Filed: Mar. 5, 2019

(65) Prior Publication Data

US 2020/0120849 P1 Apr. 16, 2020

(30) Foreign Application Priority Data

May 29, 2018 (QZ) ..... PBR 2018/1404

(51) Int. Cl.
*A01H 6/00* (2018.01)
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Haworthia* hybrid plant named 'AMIHAW1616', which is characterized by spirally-arranged, dark green and glossy foliage with near-white orbicular protuberances arranged in irregular transverse rows across the upper and lower leaf surfaces and small near-white teeth along the length of the margins. The new variety has shown to be uniform and stable in the resulting generations from asexual propagation.

4 Drawing Sheets

Latin name of the genus and species: The Latin name of the genus and species of the novel variety disclosed herein is *Haworthia limifolia* x *Haworthia pentagona.*

Variety denomination: The inventive variety of *Haworthia* hybrid disclosed herein has been given the variety denomination 'AMIHAW1616'.

CROSS REFERENCE TO RELATED APPLICATIONS

This application claims priority to the Community Plant Variety Rights application number 2018/1404, filed May 29, 2018, which is herein incorporated by reference.

BACKGROUND OF THE INVENTION

Parentage: 'AMIHAW1616' is a seedling selection resulting from the controlled pollination of an unnamed *Haworthia limifolia* plant (not patented), the seed parent, with *Haworthia pentagona* 'AMIHAW1801' (U.S. Pat. No. 30,399), the pollen parent. The crossing was made by the inventor in the autumn of 2011 at a commercial greenhouse in Heerhugowaard, the Netherlands. In the autumn of 2013, one seedling was observed which exhibited unique growth and foliage characteristics. After confirming the stability of the unique characteristics first observed, the new plant was selected for commercialization and given the name, 'AMIHAW1616'.

Asexual Reproduction: Asexual reproduction of the new cultivar 'AMIHAW1616', by way of rooting leaf cuttings, was first initiated in the summer of 2015 at the inventor's commercial greenhouse in Heerhugowaard, the Netherlands.

Through four subsequent generations, the unique features of this cultivar have proven to be stable and true to type.

SUMMARY OF THE INVENTION

The cultivar 'AMIHAW1616' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIHAW1616'. These characteristics in combination distinguish 'AMIHAW1616' as a new and distinct *Haworthia* hybrid cultivar:

1. 'AMIHAW1616' exhibits spirally-arranged succulent foliage in a basal rosette; and
2. 'AMIHAW1616' exhibits foliage with small, near-white teeth along the length of the margins; and
3. 'AMIHAW1616' exhibits dark green, glossy foliage with near-white orbicular protuberances arranged in irregular transverse rows across the upper and lower leaf surfaces.

BOTANICAL DESCRIPTION OF THE PLANT

Figure 1:
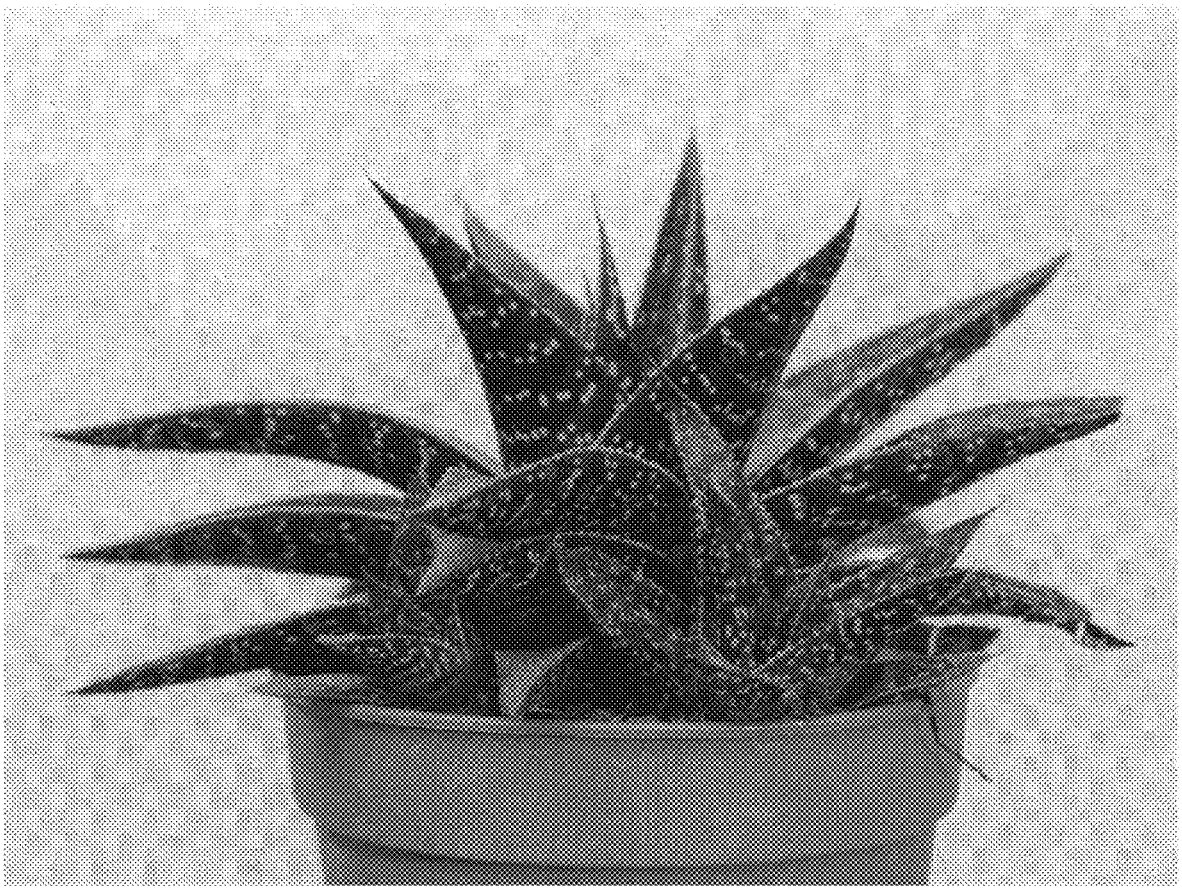
FIG. 1 illustrates, as nearly true as it is reasonably possible to make the same in color photographs of this type, an exemplary plant of 'AMIHAW1616' grown in a commercial greenhouse in Heerhugowaard, the Netherlands. This plant is approximately 12 months old, shown planted in a 12 cm container.
Figure 2:
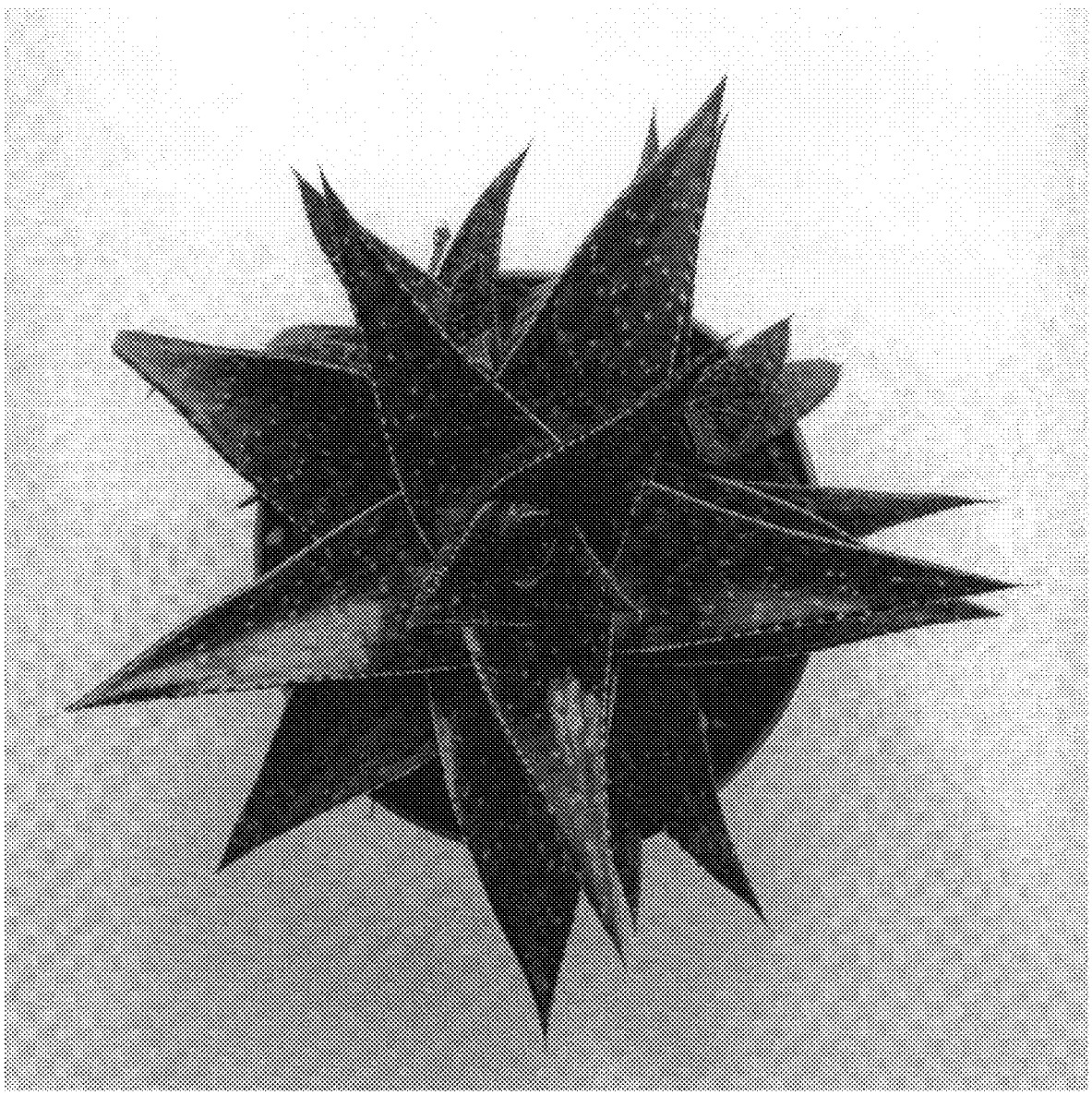
FIG. 2 illustrates, as nearly true as it is reasonably possible to make the same in color photographs of this type, the typical foliage arrangement of 'AMIHAW1616'.
Figure 3:
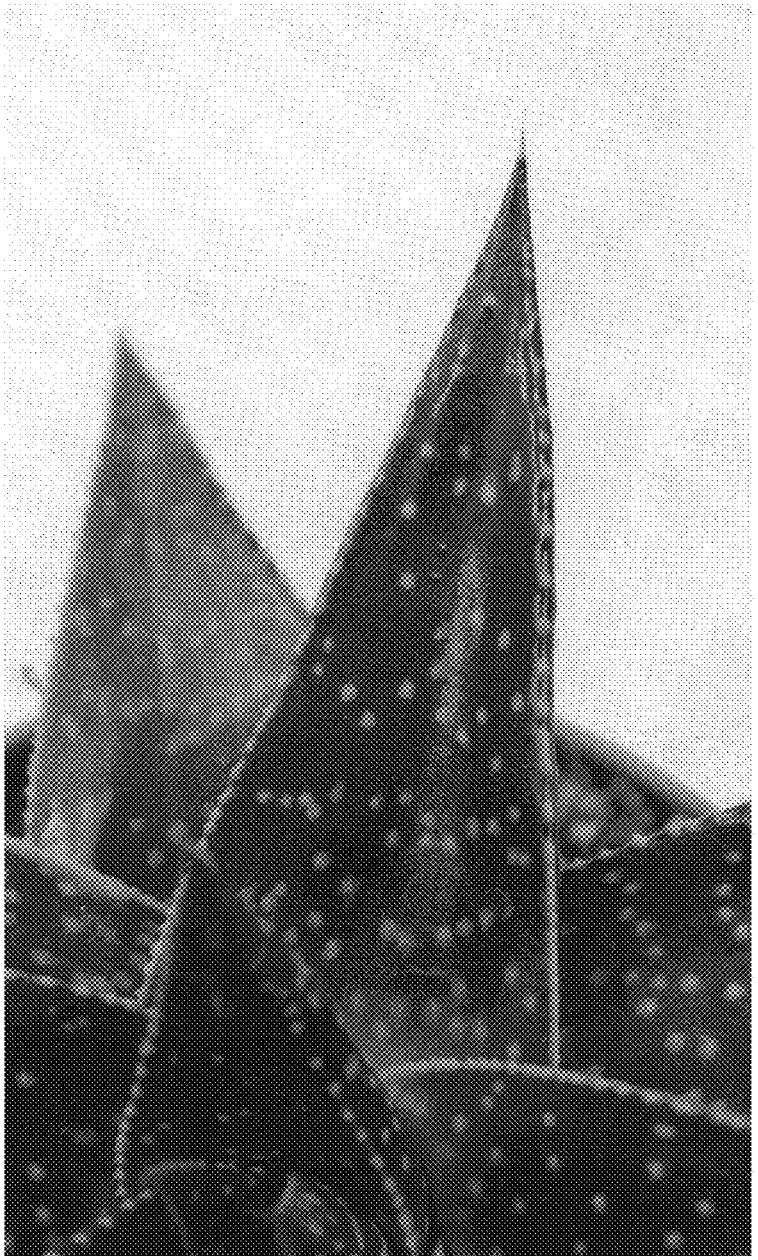
FIG. 3 illustrates, as nearly true as it is reasonably possible to make the same in color photographs of this type, the adaxial surface of the mature foliage 'AMIHAW1616'.
Figure 4:
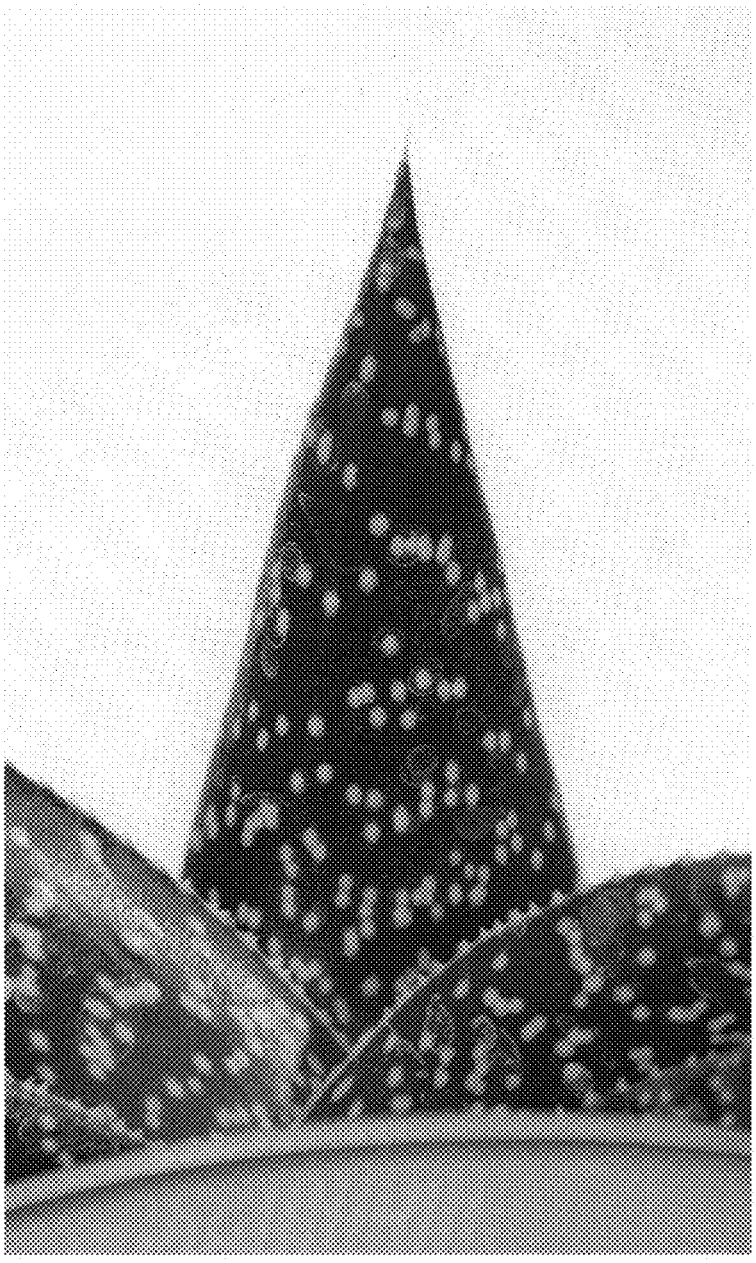
FIG. 4 illustrates, as nearly true as it is reasonably possible to make the same in color photographs of this type, the abaxial surface of the mature foliage 'AMIHAW1616'.

The following observations and measurements made in December of 2018 describe averages from a sample set of six specimens of 12 months old 'AMIHAW1616' plants grown in 12 cm nursery containers at commercial greenhouse in Heerhugowaard, the Netherlands. Plants were produced using conventional greenhouse production protocols for *Haworthia* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIHAW1616' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIHAW1616' and a comparison with the parents and closest known comparator is provided below.

Plant description:

*Growth habit*.—Succulent perennial with foliage growing in a stemless, non-branched basal rosette.

*Plant shape*.—Globular.

*Height from soil level to top of foliar plane*.—9.9 cm.

*Plant spread*.—Average of 19.2 cm.

*Growth rate*.—Slow to moderately fast.

*Plant vigor*.—Moderately vigorous.

*Propagation*.—Type — Leaf cuttings. Time to initiate rooting — Approximately 21 days at 18 degrees Celsius. Crop time — Approximately 45 weeks to produce a marketable plant in a 12 cm container.

*Disease and pest resistance or susceptibility*.—Neither resistance nor susceptibility to typical Aloe pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Spirally arranged in a rosette.

*Division*.—Simple.

*Attachment*.—Sessile.

*Quantity*.—24 leaves per rosette.

*Shape*.—Ovate to narrow deltoid succulent foliage.

*Dimensions*.—9.4 cm long, 4.0 cm wide, and 1.2 cm thick, on average.

*Aspect*.—Very slightly concaved and slightly curled downward.

*Attitude*.—Juvenile foliage at the center of the rosette is held outward; foliage becomes progressively more relaxed towards the outer whorls of mature foliage, at an average angle of 25 degrees from horizontal.

*Apex*.—Narrow acute to long apiculate, with a soft mucronate tip.

*Base*.—Broad cuneate.

*Margin*.—Finely dentate; teeth have an average length of 0.075 cm and are colored greyed-green, nearest to a mixture of RHS 190B and 190C. Margins are not undulated or lobed.

*Texture, adaxial surface*.—Glabrous and moderately covered with orbicular to broad elliptic protuberances loosely arranged in irregular transverse rows across the leaf surface; protuberances are approximately 0.15 cm high and 0.1 cm in diameter, at maturity.

*Texture, abaxial surface*.—Glabrous and moderately to densely covered with orbicular to broad elliptic protuberances loosely arranged in irregular transverse rows across the leaf surface; protuberances are approximately 0.175 cm high and 0.125 cm in diameter, at maturity.

*Luster, adaxial surface*.—Glossy.

*Luster, abaxial surface*.—Glossy.

*Color*.—Juvenile foliage, adaxial surface — Nearest to in between green and yellow-green, RHS NN137 and 147A; protuberances are colored greyed-green, nearest to RHS 191C. Juvenile foliage, abaxial surface — Green, nearest to RHS NN137A; protuberances are colored greyed-green, nearest to RHS 191C. Mature foliage, adaxial surface — Nearest to in between yellow-green and greyed-green, RHS 147A and N189A; fading to a lighter shade of yellow-green towards the base, nearest to RHS 148C; base is in between white and greyed-white, RHS N155C and 156D; protuberances are colored greyed-green, nearest to RHS 191B. Mature foliage, abaxial surface — Nearest to in between green and yellow-green, RHS 139A and 147A; fading to a lighter shade of yellow-green towards the base, nearest to RHS 146A; base is in between white and greyed-white, RHS N155C and 156A; protuberances are colored greyed-green, nearest to a mixture of RHS 191B and 191C.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIHAW1616' differ from the seed parent, an unnamed *Haworthia limifolia* (not patented), in the following characteristics described in Table 1 below.

TABLE 1

| Characteristic | 'AMIHAW1616' | *Haworthia limifolia* seed parent |
|---|---|---|
| Plant size. | Larger than the seed parent. | Smaller than 'AMIHAW1616'. |
| General coloration of the mature foliage. | Darker shade of green than the seed parent. | Lighter shade of green than'AMIHAW1616'. |
| Foliage luster. | More glossy than the seed parent. | Less glossy than 'AMIHAW1616'. |
| Leaf protuberances. | Orbicular to broad elliptic protuberances loosely arranged in irregular transverse rows. | Conspicuous transverse linear protuberances presenting as raised ribs across the leaf surface. |
| Foliage margins. | Finely dentate. | Entire. |

Plants of the new cultivar 'AMIHAW1616' differ from the pollen parent, *Haworthia pentagona* 'AMIHAW1801' (U.S. Pat. No. 30,399), in the following characteristics described in Table 2 below.

TABLE 2

| Characteristic | 'AMIHAW1616' | 'AMIHAW1801' |
|---|---|---|
| Plant size. | Smaller than 'AMIHAW 1801'. | Larger than 'AMIHAW1616'. |
| Rate of growth. | Slower than 'AMIHAW1801'. | Faster than 'AMIHAW1616'. |
| General coloration of the mature foliage. | Dark green. | Light greyed-green. |
| Foliage margins. | Finely dentate with more teeth than 'AMIHAW1801'. | Coarsely dentate with fewer teeth than 'AMIHAW1616'. |

TABLE 2-continued

| Characteristic | 'AMIHAW1616' | 'AMIHAW1801' |
|---|---|---|
| Presence of leaf protuberances. | Present. | Not present. |

COMPARISONS WITH THE CLOSEST KNOWN COMPARATOR

Plants of the new cultivar 'AMIHAW1616' differ from the closest known commercial comparator, *Haworthia maxima* 'SIHAW7026' (U.S. Pat. No. 29,693), in the following characteristics described in Table 3 below.

TABLE 3

| Characteristic | 'AMIHAW1616' | 'SI HAW 7026' |
|---|---|---|
| Plant size. | Larger than 'SI HAW 7026' | Smaller than 'AMIHAW1616'. |
| Foliage size. | Larger than 'SI HAW 7026' | Smaller than 'AMIHAW1616'. |
| Foliage attitude. | More relaxed than 'SI HAW 7026' | More upright than 'AMIHAW1616'. |
| Foliage margins. | Finely dentate. | Postulate. |
| Size of leaf protuberances. | Smaller than 'SI HAW 7026' | Larger than 'AMIHAW1616'. |
| General coloration of leaf protuberances. | Very light greyed-green, appearing as near-white. | White. |

That which is claimed is:

1. A new and distinct variety of *Haworthia* hybrid plant named 'AMIHAW1616', substantially as described and illustrated herein.

* * * * *